United States Patent [19]
Heikkila et al.

[11] Patent Number: 5,516,763
[45] Date of Patent: May 14, 1996

[54] CRYSTALLINE LACTITOL MONOHYDRATE AND A PROCESS FOR THE PREPARATION THEREOF, USE THEREOF, AND SWEETENING AGENT

[75] Inventors: Heikki O. Heikkila, Espoo; Juha V. Nurmi, Pinjainen, both of Finland

[73] Assignee: Suomen Xyrofin Oy, Kotka, Finland

[21] Appl. No.: 995,856

[22] Filed: Dec. 23, 1992

Related U.S. Application Data

[63] Continuation of Ser. No. 687,856, Jul. 29, 1991, abandoned.

[30] Foreign Application Priority Data

Dec. 1, 1988 [FI] Finland ................................ 885588
Apr. 8, 1989 [WO] WIPO ....................... PCT/FI89/00142

[51] Int. Cl.⁶ .......................... A61K 31/715; C07H 1/00; A23G 3/00; A23L 1/00
[52] U.S. Cl. ........................... 514/53; 536/1.11; 536/124; 426/658
[58] Field of Search ............................ 514/53; 536/1.11, 536/124; 426/658

[56] References Cited

FOREIGN PATENT DOCUMENTS 0039981 of 0000 European Pat. Off. .

OTHER PUBLICATIONS

J. A. Kanters, et al., "Structure of Lactitol (4–O–β–D–Galactopyranosyl–D–glucitol) Monohydrate: an Artificial Sweetner", *Acta Cryst.*, (1990), C46, pp. 2408–2411.
M. van Bommel et al, "The Crystal and Molecular Structures of Lactitol Monohydrate and Lactitol Dihydrate", Abstract (1980).
John A. Van Velthuijsen: "Food additives derived from Lactose: Lactitol Palmitate" vol. 27, No. 4, J. Agric. Food Chem., 680–86 (1979).
Cess J. Booy: "Lactitol: A new food ingredient", vol. 212, International Dairy Federation Bulletin, 62–68 (1987).
CH. den Uyl: "Technical and commercial aspects of the use of lactitol in foods as a reduced–calorie bulk sweetener," vol. 3, Developments In Sweetners–3, 65–81 (London and New York 1987).
M. L. Wolfrom, W. J. Burke, K. R. Brown and R. S. Rose, 60, J. Am. Chem. Soc. 571–573 (1938).
M. L. Wolfrom, R. M. Hann and C. S. Hudson, 75, J. Am. Chem. Soc., 1105 (1952).
Comments of George A. Jeffrey dated Apr. 24, 1992.
Comments of G. L. Nanninga dated Mar. 11, 1992.

*Primary Examiner*—Douglas W. Robinson
*Assistant Examiner*—Everett White
*Attorney, Agent, or Firm*—Kenyon & Kenyon

[57] ABSTRACT

A crystalline lactitol monohydrate having lattice cell constants a =7.815±0.008 Å, b=12.682±0.008 Å, and c=15.927±0.008 Å, and a melting range between 90° and 105° C., and a water content between 4.85 and 5.15%, as well as a process of preparing said crystalline lactitol monohydrate by evaporating the aqueous solution of lactitol to a concentration between 75 and 88% by weight, cooling the resultant mixture at a temperature ranging between 30 and 75° C., subsequently separating the lactitol monohydrate crystals from the mother liquor, and subsequently drying with air having a temperature between 120° C., and a relative humidity between 0 and 40%, for a time period less than 24 hours. The invention also relates to the use of said crystalline lactitol monohydrate as a bulk sweetener for the total or partial replacement of sucrose, in dietetic products, confectionery, bakery products, cereals, desserts, jams, beverages, chocolate, chewing gum and ice-cream, and in pharmaceuticals and cosmetic products, such as tooth paste, as well as a special sweetening agent resembling sucrose, mainly composed of said crystalline lactitol monohydrate.

10 Claims, 1 Drawing Sheet

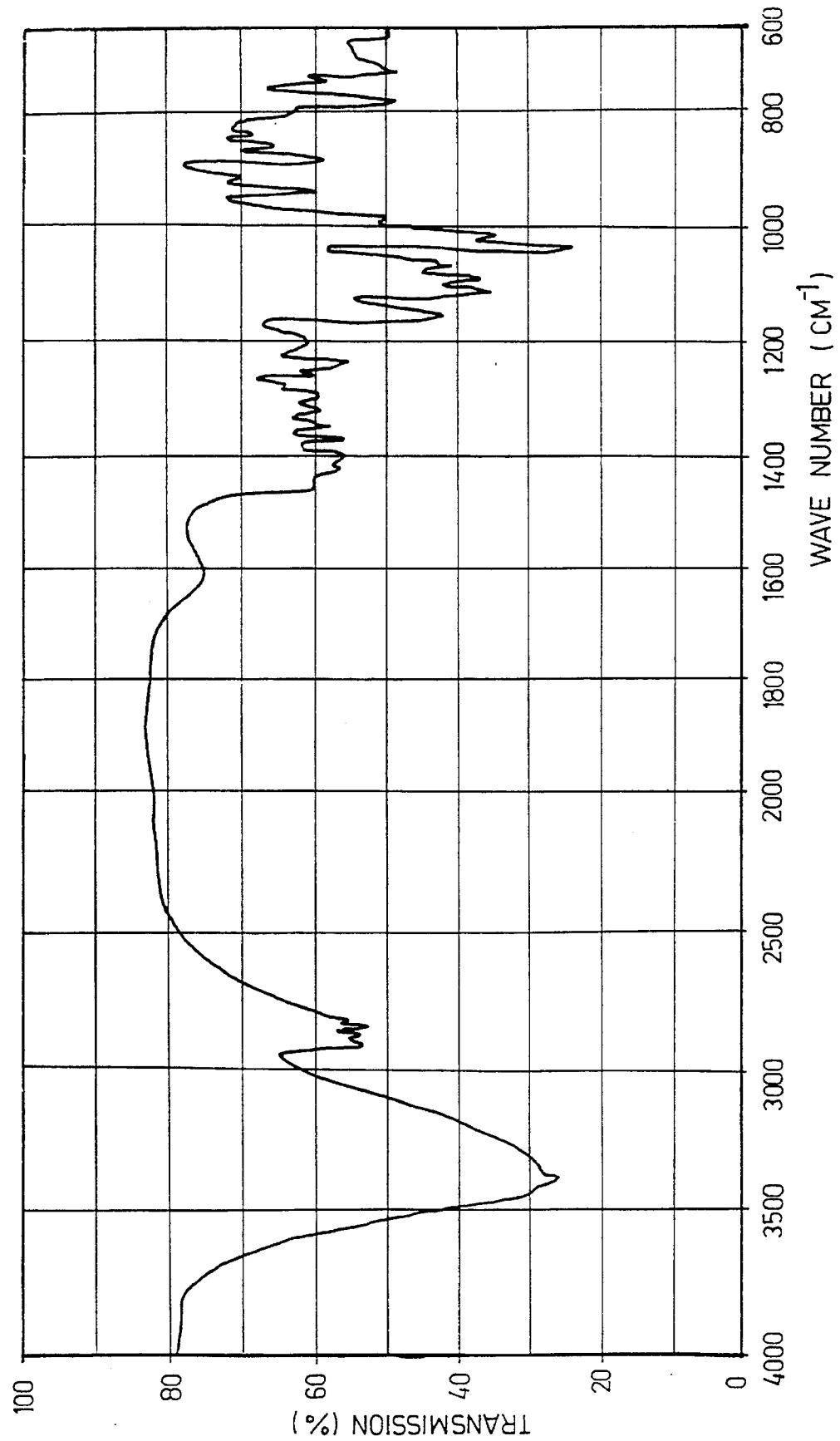

CRYSTALLINE LACTITOL MONOHYDRATE AND A PROCESS FOR THE PREPARATION THEREOF, USE THEREOF, AND SWEETENING AGENT

This application is a continuation of Ser. No. 07/687,856 filed Jul. 29, 1991, now abandoned.

The invention relates to a new crystalline lactitol monohydrate, and a process for the preparation thereof by crystallization from an aqueous solution, the use of the said new crystalline lactitol monohydrate in dietetic products, confectionery, bakery products, cereals, desserts, jams, beverages, chocolate, chewing gum and ice-cream, as well as in pharmaceutical and cosmetic products, such as tooth paste. The invention also relates to a new sweetening agent resembling sugar, mainly composed of the said new crystalline lactitol monohydrate.

Lactitol is a bulk sweetener which can be used as a total or partial replacement for sucrose, however, its energy content is only about half of that of sucrose, and it does not cause increased blood glucose content; furthermore, it is tooth-friendly (see Developments in Sweeteners, Ed. Grenby, T. H., Vol. 3, 1987, p. 65–81).

The preparation of lactitol from lactose has been known for a long time. Industrially, lactitol is prepared analogously with the preparation of sorbitol from glucose by hydrogenation in the presence of a Raney nickel catalyst. An aqueous solution of lactose, typically having a concentration between 30 and 40% by weight due to the poor solubility of lactose, is hydrogenated at 70° to 130° C. at a pressure between 30 and 74 arm. The preparation is described in Wolfrom, M. L., Burke, W. J., Brown, K. R. and Rose, R. S., J. Am. Chem. Soc. 60, (1938) p. 571–573.

Crystalline lactitol is reported to occur in anhydrous form (anhydride) as well as in the form of a monohydrate and dihydrate, which forms have been known for a long time with the exception of pure monohydrate. Among the crystal forms of lactitol, lactitol monohydrate is of considerable commercial interest on account of its low hygroscopicity.

In the preparation process mentioned above, lactitol anhydride can be crystallized by adding ethanol to a lactitol solution evaporated to a high concentration. After a crystallization time of one month, the yield of lactitol was 80%, and the melting point of the resulting crystal, which was found to be an anhydride, was between 144° and 146° C.

The crystallization of lacitol dihydrate was presumably mentioned for the first time by Senderens, J. B., Compt. Rend. 170, (1920) p. 47–50. Lactitol solution obtained by hydrogenation was evaporated slowly at room temperature so that crystallization was initiated. The melting point of the resulting product was 78° C., and Senderens mistakenly regarded it as a monohydrate. However, it appears from European Patent 0039981 and Wolfrom, M. L., Hann, R. M. and Hudson, C. S., J. Am. Chem. Soc. 74 (1952) p. 1105 that the product obtained by Senderens was a dihydrate having a moisture content of 9.5%, determined by a Karl Fisher method, and a melting point between 76° and 78° C.

The next attempt to prepare lactitol monohydrate by crystallization was made in 1979; the end product, however, was an impure dihydrate, see van Velthuijsen, J. A., J. Agric. Food Chem., 27, (1979) p. 680. The solubility of the "monohydrate" so obtained was reported to be 64% by weight at 25° C.; however, it has been proved that lactitol monohydrae cannot have such a solubility, see the above-mentioned European Patent 0039981. Taking into consideration that the alleged monohydrate was impure (4.5% of other sugars and dihydrate), the corrected solubility is the right solubility of lactitol (about 59% by weight on dry substance basis). The reported melting range from 94° to 97° C. also indicates the presence of a slightly overdried (impure) dihydrate.

Another attempt to prepare lactitol monohydrate was made in 1981, see the above-mentioned European Patent 0039981. The low crystallization temperature, however, resulted in the formation of monohydrate and dihydrate either as mixed crystals or separately, the product being then dried into partially anhydrated monohydrate. The reported melting point 121°–123° C. is that of partially anhydrated monohydrate from which the lattice cell constants of monohydrate are obtained by means of a single-crystal X-ray diffractometer within the measuring accuracy. The surface layer of partially anhydrated monohydrate may be integral (double crystal) or fragmented or it may be composed of numerous separate anhydride crystals, which becomes apparent from the high scattering of the lattice cell constants when determined by the single-crystal method. Partially anhydrated monohydrate is at least as stable as a complete anhydride which does not bind water at room temperature at moderate relative humidities.

The surface layer of said partially anhydrated monohydrate is imperfect and under suitable conditions it will be restored partially or completely to the monohydrate form. Since the formation of a perfect lattice structure is irreversible, the restored crystal structure will never be perfect, i.e. if the anhydride or partially anhydrated monohydrate takes (binds) crystal water, the product obtained does not have the crystal structure of lactitol monohydrate. Both the anhydrated and partially restored monohydrate easily get cloddy and have a rather poor flowability and rather a high hygroscopicity on account of the fragmented surface and high dust content of the product.

Monohydrate loses all of its crystal water as rapidly as in two hours when it is dried at 105° C. in a conventional laboratory oven. The melting point of the "monohydrate" disclosed in European Patent 0039981, that is, 121°–123° C., corresponds to that of a monohydrate anhydrated to a degree of anhydration of 10 to 15%. In addition, the "monohydrate" disclosed in this patent, which lost 2% of its weight at 130° C. during 3 days, is originally a monohydrate anhydrated to a degree of anhydration of 60%. The "monohydrates" disclosed in the European patent are not monohydrates anhydrated from pure monohydrate; instead, they are overdried products formed from the mixtures of dihydrate and monohydrate due to the crystallization method.

Lacitol hydrate powders anhydrated to a moisture content of less than 3% have been prepared by drying both lacitol solution and crystalline hydrate. The hygroscopicity of these powders is utilized in drying moist mixtures (European Patent Application 0231643).

The preparation of pure lactitol monohydrate having lattice cell constants a=7.815±0.008 Å, b=12.682±0.008 Å, and c=15.927±0.008 Å; and a melting range between 94° and 100° C., preferably between 94° and 98° C., has now succeeded for the first time. The melting range was determined with a Bchi Tottol melting point apparatus. The lactitol content of the said pure lactitol monohydrate is more than 99.5% on a dry substance basis, and its moisture content is between 4.85 and 5.15%.

The new lactitol monohydrate has a good flowability and long shelf life, and it is stable at room temperatures, in relative humidities ranging from 25 to 75%. After having been stored under varying atmospheric conditions for about two years in an open paper sack, the lactitol monohydrate did no become cloddy and its flowability was 5.1 s/10 g measured by a funnel technique, the inclination of the funnel being 60°, the pipe length 23 mm and the inner diameter 11 mm.

The infrared absorption of the lactitol monohydrate was measured by a Perkin-Elmer 398 spectrometer from a tablet having a composition of 1 g of lactitol monohydrate and 131 g of KBr. The infrared spectrum is shown in the drawing.

No more than 150 g of pure lactitol monohydrate on a dry substance basis dissolves in 100 ml of water at 25° C. Pure lactitol monohydrate crystals are colourless, odourless and transparent.

An accurate determination of the melting range of lacitol monohydrate can be most successfully carried out by introducing samples of milled lactitol into several capillary tubes and melting the open ends of the tubes before measuring. The measurements are carried out with a conventional melting point apparatus at different constant temperatures using one capillary tube per measurement until the extreme points of the melting range are found.

When determining the melting point, one must take into account that molten lactitol monohydrate has a high viscosity at its melting temperature, wherefore it takes time (even 2 minutes) before the sample is spread evenly on the walls of the capillary tube. Furthermore, the melt often contains bubbles caused by the liberation of crystal water, which remain in the melt for a long time.

In the process according to the above-mentioned European Patent 0039981, lactitol monohydrate anhydride is prepared by crystallizing lacitol within the temperature range from 10° to 50° C. from a seeded lactitol solution obtained by hydrogenation and evaporated to a concentration between 70 and 85% or from a mother liquor obtained from the first crystallization step. This process can be used for the crystallization of lactitol only when the purity of lactitol in the feed solution is high, and since dihydrate may already be crystallized from pure lactitol solution, the crystallization of pure monohydrate is difficult if not impossible.

In the crystallization process according to the invention, crystallization temperatures (in the range from 80° to 30° C.) are considerably higher than in the prior art process (from 50° to 10° C.), whereby it is possible to crystallize lactitol monohydrate in at least four successive crystallization steps. With the present new process the total yield of lactitol monohydrate (see the crystallization series of Example 1, wherein the total yield is 97.6% on lactitol) is considerably higher than can be achieved with the prior art process (no more than 85% on lactitol).

The crystallization tests showed that if the crystallization is to occur in a controlled manner for obtaining a desired crystal size without a wide crystal size distribution, the crystallization should be effected in such a manner that the supersaturation of the mother liquor remains below 1.3 (preferably 1.2) with respect to lactitol throughout the crystallization. The supersaturation can be maintained within a desired range either by using a sufficiently long crystallization time or by measuring the dry substance content of the mother liquor with a refractometer. The supersaturation can be calculated from the dry substance content of the mother liquor and from the solubility curve of lactitol. The supersaturation (s) is defined as follows:

$$s = \frac{Cml \cdot (100 - Cml')}{Cml' \cdot (100 - Cml)}$$

$Cml$ = measured dry substance content of mother liquor, % by weight
$Cml'$ = solubility of lactitol in the mother liquor Tests carried out and their results Monohydrate anhydride (Lacty-M, LCDE-31) partially restored during storage and having a melting range 97°–103° C. corresponding to 2% anhydration was cloddy and possessed a hygroscopity substantially greater than that of the monohydrate (from Test 2 in Example 1). Water absorptions at 20° C. after storage for 3 days at various relative humidities are shown in the following Table I.

TABLE I

| | Hygroscopicity comparison | |
| --- | --- | --- |
| f | Monohydrate (Example 1, Test 2) | Lacty-M LCDE-31 |
| 75% | 0.05 wt % | 0.2 wt % |
| 85% | 0.2 wt % | 0.5 wt % |
| 95% | 2.5 wt % | 3.3 wt % | f = relative humidity of ambient air, %.

Drying tests were carried out on lactitol monohydrate in a conventional laboratory oven at a pressure of 1 bar. The samples were weighed and the degree of anhydration was calculated as a function of the drying time. Table II shows the degree of anhydration under varying drying conditions.

TABLE II

| | Anhydration tests Drying Degree of anhydration (%) | | | | | | |
| --- | --- | --- | --- | --- | --- | --- | --- |
| time (h) | 1 20° C. 0% | 2 40° C. 25% | 3 60° C. 15% | 4 70° C. 10% | 5 80° C. 5% | 6 90° C. <5% | 7 105° C. <5% |
| 0 | 0 | 0 | 0 | 0 | 0 | 0 | 0 |
| 1 | — | — | 2 | 4 | 8 | 34 | 78 |
| 2 | — | — | 4 | 10 | 26 | 86 | 100 |
| 4 | — | — | 6 | 20 | 78 | 100 | — |
| 24 | 0.08 | — | — | — | 98 | — | — |
| 55 | — | 0.3 | — | — | — | — | — |
| 72 | 4.1 | — | 86 | 96 | — | — | — |
| 121 | — | — | 94 | 100 | — | — | — |
| 142 | — | 0.4 | — | — | — | — | — |
| 144 | 12 | — | — | — | — | — | — |
| 219 | 21 | — | — | — | — | — | — |
| 338 | 38 | — | — | — | — | — | — |

1) sample of 10 g at 20° C. when f = about 0%,
2) sample of 10 g at 40° C. when f = about 25%,
3) sample of 200 g at 60° C. when f = about 15%,
4) sample of 200 g at 70° C. when f = about 10%,
5) sample of 200 g at 80° C. when f = about 5%,
6) sample of 200 g at 90° C. when f < 5%,
7) sample of 200 g at 105° C. when f < 5%,
f = relative humidity of ambient air, %

The melting ranges of the partially anhydrated monohydrates formed in the test are 100°–146° C. (cf. Example 3).

On account of its excellent technical and physiological properties, the new lactitol monohydrate is particularly suitable as a substitute for sugar in diabetic, dietetic or tooth-friendly products. By combining lactitol monohydrate with other bulk or intense sweeteners, such as saccharin, Aspartame, Acesulfame K, Alitane, Sucralose, Stevioside or xylitol, a product highly resembling sugar and yet having a lower energy content and further being tooth-friendly can be prepared. Also this product is novel, and can be used instead of sugar e.g. in sugar products, confectionery, jams, bakery products, table-top sweeteners, cereals, dessers, chocolate, beverages, chewing gum and icecreams, as well as in pharmaceutical and cosmetic products, such as toothpaste.

EXAMPLE 1

Cooling crystallization

A four-step crystallization test sequence was carried out on lactitol monohydrate, starting from a filtered and de-ionised lactitol solution. The lactitol solution had been prepared from a lactose solution hydrogenated by the conventional technique.

All of the nine crystallization tests of this Example were carried out analogously with Test 1 which was performed in the following manner:

The crystallization was carried out according to the following steps: A lactitol solution having a purity of 98.3% lactitol in the dry matter was evaporated to 82.1% by weight at a temperature above 70° C., and 423 kg thereof was transferred into a crystallizer. The crystallizer was a conventional horizontal cylindrical batch-operated cooling crystallizer having a volume of 0.4 m$^3$ and provided with a mixer and a recycling water jacket whose temperature was controlled by means of a microprocessor. In the crystallizer, the temperature of the solution was adjusted to 70° C., whereafter the solution was seeded with ground lactitol monohydrate crystals. The seed crystal size was 0.02–0.05 mm, and the quantity thereof was 0.004% by weight on the lactitol in the batch. After the seeding, the mass was cooled in 16 hours down to 40° C., first slowly and ultimately more rapidly.

When the crystallization was complete the crystals were separated from the mother liquor with a conventional basket centrifuge wherein the crystals were also washed using 9.2% of water per obtained amount of crystal product. The centrifuged crystals were dried with a drum dryer using the conventional technique. The diameter of the cocurrent drum dryer used was 0.6 m, height 2.5 m and inclination about 1°; the speed of rotation was 3.5 rpm and the temperature of the drying air was 95° C. The feed rate of lactitol monohydrate was about 1.2 kg/min and the delay time about 30 minutes.

The performance conditions and results of the crystallization tests are presented in Tables III and IV hereinafter.

The total yield of lactitol monohydrate (four-step crystallization) was 97.6%.

TABLE III

| | Performance conditions of cooling crystallization tests | | | | | | | | |
|---|---|---|---|---|---|---|---|---|---|
| Test | 1 | 2 | 3 | 4 | 5 | 6 | 7 | 8 | 9 |
| Step | I | I | I | I | I | II | II | III | IV |
| a | 423 | 392 | 422 | 453 | 353 | 443 | 361 | 320 | 126 |
| b | 82.1 | 83.1 | 82.3 | 82.5 | 82.5 | 81.5 | 83.1 | 85.7 | 86.0 |
| c | 98.3 | 98.5 | 98.2 | 98.8 | 97.9 | 96.5 | 95.3 | 91.3 | 81.2 |
| d | 0.004 | 0.005 | 0.004 | 0.004 | 0 | 0.004 | 0.009 | 0.007 | 0.014 |
| e | 70 | 70 | 70 | 71 | 70 | 67 | 70 | 70 | 70 |
| f | 40 | 40 | 40 | 40 | 40 | 37 | 40 | 40 | 40 |
| g | 16 | 16 | 32 | 16 | 32 | 15 | 17 | 40 | 110 |
| h | 9.2 | 11.1 | 9.5 | 9.4 | 7.8 | 14.2 | 13.8 | 19.0 | 19.5 | a total amount of mass to be crystallized at the time of seeding, kg
b dry matter content of mass at the time of seeding, % by weight
c lactitol purity of mass, % by weight on dry matter
d amount of seeds, % by weight on lactitol in the mass
e seeding temperature, °C.
f final temperature of crystallization, °C.
g crystallization time, h
h amount of washing water, % by weight per product crystal

TABLE IV

| | Results of cooling crystallization tests | | | | | | | | |
|---|---|---|---|---|---|---|---|---|---|
| Test | 1 | 2 | 3 | 4 | 5 | 6 | 7 | 8 | 9 |
| Step | I | I | I | I | I | II | II | III | IV |
| a | 55.4 | 49.8 | 53.0 | 54.2 | 60.3 | 56.0 | 58.6 | 60.8 | 53.8 |
| b | 99.9 | 99.7 | 99.9 | 99.9 | 100 | 99.6 | 99.5 | 99.4 | 97.5 |
| c | 95.0 | 95.0 | 95.0 | 95.1 | 95.0 | 95.0 | 95.0 | 95.0 | 95.0 |
| d | 0.68 | 0.55 | 0.41 | 0.49 | 0.39 | 0.42 | 0.41 | 0.35 | 0.31 |
| e | 45 | 42 | 39 | 34 | 35 | 33 | 32 | 26 | 23 |
| f | 94–98 | 94–98 | 94–98 | 94–98 | 94–98 | 94–98 | 93–96 | 92–95 | 91–94 | a crystal yield after drying, % by weight on lactitol
b lactitol purity of product crystal, % by weight on dry matter TABLE IV-continued

| | Results of cooling crystallization tests | | | | | | | | |
|---|---|---|---|---|---|---|---|---|---|
| Test | 1 | 2 | 3 | 4 | 5 | 6 | 7 | 8 | 9 |
| Step | I | I | I | I | I | II | II | III | IV | c dry matter content of product crystal, % by weight
d average crystal size of product crystal, mm
e standard deviation from average size of product crystal, %
f melting range of product crystal, °C.

Crystallization Example 1 is intended to illustrate the practicability of the novel process, but the crystallization may also be carried out by modifying it in a manner as required by normal effective production operation. Thus the crystallization may also be performed without adding seed crystals, i.e. by allowing the solution to form seeds spontaneously as in crystallization test 5. Further, the crystallization may be effected entirely or partially by evaporative crystallization as demonstrated in Example 2. The crystallization may also be carried out in a continuous operation as long as the temperature is maintained in the range 80° C.–30° C. and the supersaturation of the mother liquor is maintained below 1.3.

EXAMPLE 2

Evaporation crystallization

Crystallization of lactitol monohydrate was performed starting from a lactitol solution prepared by hydrogenation (the same as in Example 1). The solution was evaporatively crystallized for 5 hours at 60° C., whereafter the crystals were separated from a slightly cooled mass, washed, and dried, as explained in the following.

The lactitol solution was concentrated in a conventional 0.4 m$^3$ evaporation crystallizer at 60° C. at a pressure of about 180 mbar until the dry matter content of the solution was 80.9% by weight and there was approximately 30% of solution on the volume of the crystallizer, at which point the solution was seeded with lactitol monohydrate seed crystals. The amount of seed crystals was 0.008% by weight of the lactitol monohydrate content of the final batch, and the average size of the seed crystals was about 0.03 mm. After the seeding, more feed solution was supplied to the crystallizer, and the evaporation was continued at 59°–65° C. so that the dry matter content of the mother liquor was in the range 78–82% by weight.

After evaporating for 5 hours, the crystallizer was replete with a mass which was transferred into a cooling crystallizer and cooled from 62° C. to 55° C. in 10 hours, whereafter the crystals were separated from the mother liquor by centrifuging and dried as in Example 1. The crystal yield was 49.7% on lactitol. The purity of the lactitol monohydrate product was 99.7% on a dry matter basis, the dry matter content was 95.0% and the melting range 94.5°–98° C.

EXAMPLE 3

Anhydration of monohydrate

The lactitol monohydrate produced in Test 2 of Example 1 was dried at 20°–105° C. with drying air having a relative humidity of 0–25% for varying periods of time, whereby different partially anhydrated monohydrates were obtained. The melting range of the anhydrated monohydrates obtained is shown as a function of the degree of anhydration in Table V:

TABLE V

| | | Melting ranges | | |
|---|---|---|---|---|
| Ds | An | Mp' | Mp | |
| 95.00 | 0 | 94 | 98 | monohydrate |
| 95.15 | 3 | 100 | 105 | |
| 95.25 | 5 | 103 | 118 | |
| 96.10 | 22 | 113 | 128 | |
| 98.40 | 68 | 129 | 140 | |
| 99.10 | 82 | 138 | 143 | |
| 100.00 | 100 | 144 | 146 | anhydride |

Ds = dry matter content of product, % by weight
An = degree of anhydration, i.e. amount of removed crystal water, %
Mp' = starting point for melting, °C.
Mp = melting point, °C.

Like Example 1, Examples 2 and 3 are intended to illustrate the invention, but the crystallization can be carried out also by modifying it in a manner as required by normal effective production operation, as explained hereinabove.

EXAMPLE 4

Lactitol plain chocolate

| | g |
|---|---|
| Cocoa butter | 165 |
| Cocoa liquor | 630 |
| Lactitol monohydrate | 719 |
| Acesulfame K | 2.3 |
| Vanillin | 0.3 |
| Lecithin | 6 |

Procedure: Conch. 17 hours at 50° C. and 3 hours at 60° C.

EXAMPLE 5

Lactitol milk chocolate

| | g |
|---|---|
| Cocoa butter | 345 |
| Cocoa liquor | 195 |
| Milk powder, fat 26% | 209 |
| Lactitol monohydrate | 789 |
| Acesulfame K | 1.4 |
| Vanillin | 0.3 |
| Lecithin | 6 |

Procedure: Conch. 20 hours at 50° C.

Example 6

Lactitol chewy toffee

|  | g |
|---|---|
| Lactitol monohydrate | 306 |
| Finmalt L (maltitol syrup) | 306 |
| Acesulfame K | 0.2 |
| Vegetable fat | 39 |
| Emulsifier (Glycerylmonostearate) | 3 |
| Gelatine | 12 |
| Water | 25 |
| Citric acid | 8 |
| Flavour, colour | 1.5 |

Procedure:
1. Mix lactitol monohydrate, Finmalt L, vegetable fat and emulsifier.
2. Heat to 120° C.
3. Add dissolved gelatine.
4. Add citric acid, flavour and colour.
5. Pull the mass 2–4 minutes.
6. Form the mass.

EXAMPLE 7

Lactitol gelatine jelly

|  | g |
|---|---|
| Lactitol monohydrate | 200 |
| Finmalt L (maltitol syrup) | 267 |
| Acesulfame K | 0.63 |
| Water | 50 |
| Gelatin 250 BL | 35 |
| Water | 70 |
| Citric acid (50% solution) | 5 |
| Flavour, colour as required |  |

Procedure:
1. Mix lactitol monohydrate, Finmalt L, Acesulfame K and water.
2. Heat to 116° C.
3. Cool to 90° C. and add dissolved gelatine.
4. Add citric acid, flavour and colour.
5. Deposit into starch moulds.

EXAMPLE 8

Lactitol pectin jelly

|  | g |
|---|---|
| Pectin (HM confectionery) | 15 |
| Lactitol monohydrate | 50 |
| Acesulfame K | 0.7 |
| Water | 200 |
| Sodium citrate | 4 |
| Citric acid | 3.7 |
| Lactitol monohydrate | 265 |
| Finmalt L (maltitol syrup) | 630 |
| Citric acid (50 % solution) | 8.5 |
| Flavours, colours | 2.5 |

Procedure:
1. Homogenise pectin and lactitol monohydrate.
2. Add a solution of water, sodium citrate and citric acid.
3. Heat to 100° C.
4. Add a homogenised mixture of lactitol monohydrate, Acesulfame K, Finmalt L, flavours and colours.
5. Heat to 106–108° C.
6. Add citric acid.
7. Deposit into starch or plastic moulds.

EXAMPLE 9

Lactitol gum-arabic pastille

|  | g |
|---|---|
| Gum arabic, 50% solution | 400 |
| Lactitol monohydrate | 220 |
| Finmalt (maltitol syrup) | 107 |
| Acesulfame K | 1.0 |
| Water | 100 |
| Citric acid (50% solution) | 10 |
| Flavour, colour | 2 |

Procedure:
1. Mix lactitol and Finmalt to the water.
2. Heat to 120° C.
3. Add heated solution to gum arabic solution.
4. Add acid, flavour and colour.
5. Deposit into starch moulds.
6. Dry 48–60 hours at 60° C.

EXAMPLE 10

Lactitol hard candy

|  | g |
|---|---|
| Lactitol monohydrate | 368 |
| Finmalt L (maltitol syrup) | 200 |
| Acesulfame K | 0.4 |
| Water | 100 |
| Flavours, colour | 2 |

Procedure:

1. Heat sweeteners and water to 160–162° C.
2. Keep the mass 10 minutes in vacuum (0.8–0.9 . . . ).
3. Cool the mass and mix flavours and colours.
4. Form the mass.

EXAMPLE 11

Lactitol strawberry jam

|  | g |
|---|---|
| Strawberries | 300 |
| Water | 300 |
| Pectin (Obi Violettband B) | 6 |
| Lactitol monohydrate | 500 |
| Citric acid (50% solution) | 3 |
| Calcium citrate | 0.2 |
| Calcium lactate | 0.3 |
| Potassium sorbate | 1.7 |

Procedure:

1. Dry mix the pectin and 50 g of the lactitol.
2. Heat the fruit and water for few minutes.
3. Sprinkle the pectin/lactitol mixture into the fruit/-water mixture.
4. Bring to boil and keep boiling for a moment to dissolve the pectin completely.
5. Add remainder of the lactitol and boil for a little while.
6. Add the preservative and the calcium salts soluted in a small amount of water.
7. Boil until the weight of the batch is 1000 g or until desired solid content is reached.

EXAMPLE 12

Lactitol biscuits

|  | g |
|---|---|
| Lactitol monohydrate | 95 |
| Fructose | 95 |
| Fat | 10 |
| Whole egg | 50 |
| Flour | 175 |
| Fibre (oat bran) | 30 |
| Sodium bicarbonate | 7.5 |
| Salt | 1.5 |
| Ginger | 1 |
| Water | 40 |

Procedure:

1. Cream fat with lactitol and fructose.
2. Mix eggs in one by one.
3. Shift together dry ingredients and add beating throughly.
4. Cool a few hours or overnight.
5. Bake in 170° C. for about 11 minutes.

EXAMPLE 13

Chocolate cake

|  | g |
|---|---|
| Lactitol monohydrate (milled) | 179.5 |
| Butter | 180.0 |
| Whole egg | 180.0 |
| Flour | 150.0 |
| Cocoa powder | 30.0 |
| Saccharin | 0.5 |

Procedure:

1. Dry mix the milled lactitol monohydrate with the saccharin.
2. Cream with the butter until light and fluffy.
3. Gradually beat in the eggs.
4. Fold in the flour and cocoa powder.
5. Deposit into a greased cake tin (16 cm diameter).
6. Bake for 60 minutes at 180° C.

EXAMPLE 14

Fatless sponge cake

|  | g |
|---|---|
| Lactitol monohydrate (milled) | 89.3 |
| Eggs (separated) | 180 |
| Flour | 90 |
| Saccharin | 0.2 |

Procedure:

1. Dry mix the milled lactitol with the saccharin.
2. Whisk egg yolks with lactitol mixture until thick and creamy.
3. Whisk egg whites until firm and dry.
4. Fold egg white into egg yolk mixture.
5. Fold in flour.
6. Deposit into a greased and floured cake tin (16 cm diameter).
7. Bake for 40 minutes at 180° C.

Results:
Baked cake had golden colour and even crumb texture:

| Weight | 275 g |
|---|---|
| Height | 3.7 cm |
| Volume | 744 cm |
| Density | 0.37 g/ml |

EXAMPLE 15

Ice cream

|  | g |
|---|---|
| Lactitol monohydrate | 140 |
| Butterfat | 80 |
| Skimmed milk powder | 110 |
| Water | 660 |
| Emulsified (stabiliser) (Grindstaad SE 33) | 8.1 |
| Aspartame | 0.4 |
| Colour (Bush Boake Allen Permucol egg yellow powder) | 0.06 |
| Vanilla flavour | 0.4 |

Procedure:

1. Dissolve the lactitol and skimmed milk powder in the water (reserving about 5% to dissolve the aspartame).
2. Add the butterfat and emulsifier (stabiliser).
3. Pasteurise at 72° C. for 10 minutes.
4. Homogenise.
5. Rapidly cool to 5° C. and age overnight at 2–4° C.
6. Add colour, flavour and pre-dissolved aspartame.
7. Freeze to 100% overrun.

EXAMPLE 16

Frozen dessert

|  | g |
|---|---|
| Lactitol monohydrate | 100 |
| Fructose | 40 |
| Butterfat | 40 |
| Skimmed milk powder | 110 |
| Water | 700 |
| Emulsifier (stabiliser) (Grindstaad SE 33) | 9.3 |
| Aspartame | 0.24 |
| Colour (Bush Boake Allan Permucol egg yellow powder) | 0.06 |
| Vanilla flavour | 0.4 |

Procedure:

1. Dissolve the lactitol, fructose and skimmed milk powder in most of the water (reserving about 5% to dissolve the aspartame).
2. Add the butterfat and emulsifier (stabiliser).
3. Pasteurise at 72° C. for 10 minutes.
4. Homogenise.
5. Rapidly cool to 5° C. and age overnight at 2–4° C.
6. Add the colour, flavour and pre-dissolved aspartame.
7. Freeze to 100% overrun.

EXAMPLE 17

Sorbet

|  | g |
|---|---|
| Lactitol monohydrate | 250 |
| Strawberry puree | 150 |
| Gelatin 125° Bloom | 10 |

-continued

| | |
|---|---|
| Citric acid (50%) | 4.0 |
| Aspartame | 0.8 |
| Colour (Hexacol Strawberry Red) | 0.3 |
| Strawberry flavour | 1.1 |
| Water | 584 |

Procedure:

1. Dissolve the lactitol in the water.
2. Add the gelatin and mix.
3. Pasteurise at 72° C. for 10 minutes.
4. Rapidly cool to 5° C. and age overnight at 2–4° C.
5. Add strawberry puree, citric acid, colour and flavour.
6. Freeze to 65% overrun.

EXAMPLE 18

Table-top sweetener
(Equivalent sweetness to sugar)

| | g |
|---|---|
| Lactitol monohydrate | 100 |
| Sodium saccharin | 0.23 |

Procedure:

Dry mix using a ribbon blade (or other suitable dry powder mixer) until a uniform dispersion is obtained.

Application:

Suitable for direct replacement of succrose in all applications.

EXAMPLE 19

Table-top sweetener
(4 times as sweet as sugar)

| | g |
|---|---|
| Lactitol monohydrate | 100 |
| Acesulfame K | 1.85 |

Procedure:

Dry mix using a ribbon blade (or other suitable dry powder mixer) until a uniform dispersion is obtained.

Applications:

Suitable for use in reduced caloric formulations where some bulk is needed.

EXAMPLE 20

Table-top sweetener
(10 times as sweet as sugar)

| | g |
|---|---|
| Lactitol monohydrate | 100 |
| Aspartame | 6.0 |

Procedure:

Dry mix using a ribbon blade (or other suitable dry powder mixer) until a uniform dispersion is obtained.

Applications:

Suitable for sprinkling or use in low caloric formulations where bulk is not required.

EXAMPLE 21

Drinking chocolate

| | g |
|---|---|
| Lactitol monohydrate | 200 |
| Skimmed milk powder | 70 |
| Fat reduced cocoa powder | 12 |

Procedure:

Reconstitute with 708 g hot water (total 1000 g).

We claim:

1. A substantially pure crystalline lactitol monohydrate having lattice cell constants a=7.815±0.008 Å, b=12.682±0.008 Å, and c=15.927±0.008 Å, and a melting range between 90° and 105° C.

2. The crystalline lactitol monohydrate according to claim 1, further comprising a water content between 4.85 and 5.15%.

3. The crystalline lactitol monohydrate according to claim 1, which comprises a ability better than 25 s/100 g, calculated by a funnel technique, the inclination of the funnel being 60°, the pipe length 23 mm and the-inner diameter 11 mm.

4. The crystalline lactitol monohydrate according to claim 1, further comprising a hygroscopicity which is less than 0.2% w/w/ humidity after 3 days at 20° C. and 75% relative humidity.

5. The crystalline lactitol monohydrate according to claim 1 having a melting point in the range of about 94° to 98° C.

6. The crystalline lactitol monohydrate according to claim 1 which comprises a flowability better than 10 s/100 g calculated by a funnel technique, the inclination of the funnel being 60°, the pipe length 23 mm and the inner diameter 11 mm.

7. The crystalline lactitol monohydrate according to claim 1 which further comprises a hygroscopicity of less than about 0.1% w/w/ humidity after 3 days at 20° C. and 75% relative humidity.

8. A sweetening agent comprising: (i) at least about 50% of said sweetening agent being a crystalline lacititol monohydrate having lattice cell constants a=7.815±0.008 Å, b=12.782±0.008 Å and c=15.927±0.008 Å, and a melting range between 90° and 105° C.; and (ii) 0 to about 50% of a tooth-friendly sweetening agent.

9. A process of preparing a composition for ingestion by a person comprising adding to an ingredient admixture an amount of crystalline lactitol monohydrate having lattice cell constants a=7.815±0.008 Å, b=12.682±0.008 Å, and c=15.927±0.008 Å, and a melting range between about 90° and 105° C.

10. A lactitol monohydrate substantially free of lactitol in other hydration states having a melting point between about 94° and 98° C., a solubility in 25° C. water of between about 59 and 60%, and a water content between about 4.85 and 5.15%.

* * * * *